(12) United States Patent
Beckmann et al.

(10) Patent No.: US 7,141,707 B2
(45) Date of Patent: Nov. 28, 2006

(54) PROCESS FOR SEPARATING 2-BUTANOL FROM TERT-BUTANOL/WATER MIXTURES

(75) Inventors: Andreas Beckmann, Recklinghausen (DE); Dieter Reusch, Marl (DE); Franz-Felix Kuppinger, Marl (DE)

(73) Assignee: OXENO Olefinchemie GmbH, Marl (DE)

( * ) Notice: Subject to any disclaimer, the term of this patent is extended or adjusted under 35 U.S.C. 154(b) by 464 days.

(21) Appl. No.: 10/805,256

(22) Filed: Mar. 22, 2004

(65) Prior Publication Data
US 2004/0236159 A1   Nov. 25, 2004

(30) Foreign Application Priority Data
Mar. 22, 2003   (DE) ................ 103 12 916

(51) Int. Cl.
  C07C 27/26   (2006.01)
  C07C 29/74   (2006.01)
  B01D 15/00   (2006.01)
  B01D 3/00    (2006.01)

(52) U.S. Cl. ............. 568/913; 210/640; 203/39
(58) Field of Classification Search ............. None
  See application file for complete search history.

(56) References Cited

OTHER PUBLICATIONS

Chemical Abstracts, AN 1988-173020, XP-002279776, JP 62-270537, Nov. 24, 1987.
Chemical Abstracts, AN 1975-605762, XP-002279771, JP 50-016339, Jun. 12, 1975.
Guo Yufeng, et al., "Processes of s - Butanol Produced by Catalytic Hydration of n - Butene," Petrochemical Technologies and Applications, 17, 2, 1999, pp. 114-117.

*Primary Examiner*—Sikarl A. Witherspoon
(74) *Attorney, Agent, or Firm*—Oblon, Spivak, McClelland, Maier & Neustadt, P.C.

(57) ABSTRACT

The present invention relates to a process for separating 2-butanol from tert-butanol/water mixtures using a membrane to reduce a water concentration to less than the limit concentration of the distillation boundary line connecting the two azeotropes TBA/water and SBA/water and is subsequently worked up by distillation.

20 Claims, 4 Drawing Sheets

PROCESS FOR SEPARATING 2-BUTANOL FROM TERT-BUTANOL/WATER MIXTURES

BACKGROUND OF THE INVENTION

1. Field of the Invention

The present invention relates to a process for separating 2-butanol from tert-butanol/water mixtures which are obtained in the dissociation of tert-butanol (TBA), in particular tert-butanol prepared from industrial C4-hydrocarbon mixtures, into isobutene and water.

2. Discussion of the Background

Isobutene is a starting material for the production of butyl rubber, polyisobutylene, isobutene oligomers, branched C5-aldehydes and C5-carboxylic acids. It is also used as an alkylating agent and as intermediate for the preparation of peroxides.

In industrial streams, isobutene is present together with saturated and unsaturated C4-hydrocarbons. Isobutene cannot be separated economically from these mixtures by distillation because of the small boiling point difference or the very low separation factor between isobutene and 1-butene. Isobutene is therefore isolated from industrial hydrocarbon mixtures by converting isobutene into a derivative which can easily be separated off from the remaining hydrocarbon mixture and redissociating the isolated derivative into isobutene and the derivative-forming agent.

The following procedure is usually employed to separate isobutene from C4 fractions, for example the C4 fraction from a steam cracker. After the major part of the multiply unsaturated hydrocarbons, mainly butadiene, has been removed by extraction (or extractive distillation) or selective hydrogenation to linear butenes, the remaining mixture (raffinate I or hydrogenated cracking C4) is reacted with alcohol or water. Use of methanol as alcohol gives methyl tert-butyl ether (MTBE) and use of water gives tert-butanol (TBA). After they have been separated off, both products can be dissociated to give isobutene in a reversal of their formation.

The dissociation of TBA is easier to carry out than the dissociation of MTBE and gives smaller amounts of by-products and is thus the preferred method of isolating isobutene. The dissociation of TBA is preferably carried out in the gas or liquid phase in the presence of an acid with partial conversion of TBA.

If isobutene-containing hydrocarbon streams in which linear butenes are also present are used for preparing TBA from isobutene, small amounts of 2-butanol (SBA) are also formed.

Whether this presents any further problem depends on how the resulting reaction mixture is worked up to give pure TBA or a TBA/water azeotrope. Owing to the low 2-butanol content of the reaction mixture, the maximum permissible 2-butanol concentration of, for example, 0.2% by mass in the TBA or in the TBA/water azeotrope is not exceeded.

If, however, the industrial TBA or TBA/water azeotrope is partially dissociated into isobutene and water, separating off the isobutene formed results in a TBA/water mixture enriched in 2-butanol (SBA). This mixture is unsuitable for the preparation of commercial quality TBA or TBA/water azeotrope without 2-butanol being separated off. It is likewise not practical to prepare isobutene from this mixture, because an increasing 2-butanol content also results in an increase in the concentration of linear butenes in the isobutene, so that the specification of the latter cannot be achieved. It is therefore necessary to discharge part of the 2-butanol while avoiding losses of TBA.

Figure 1:
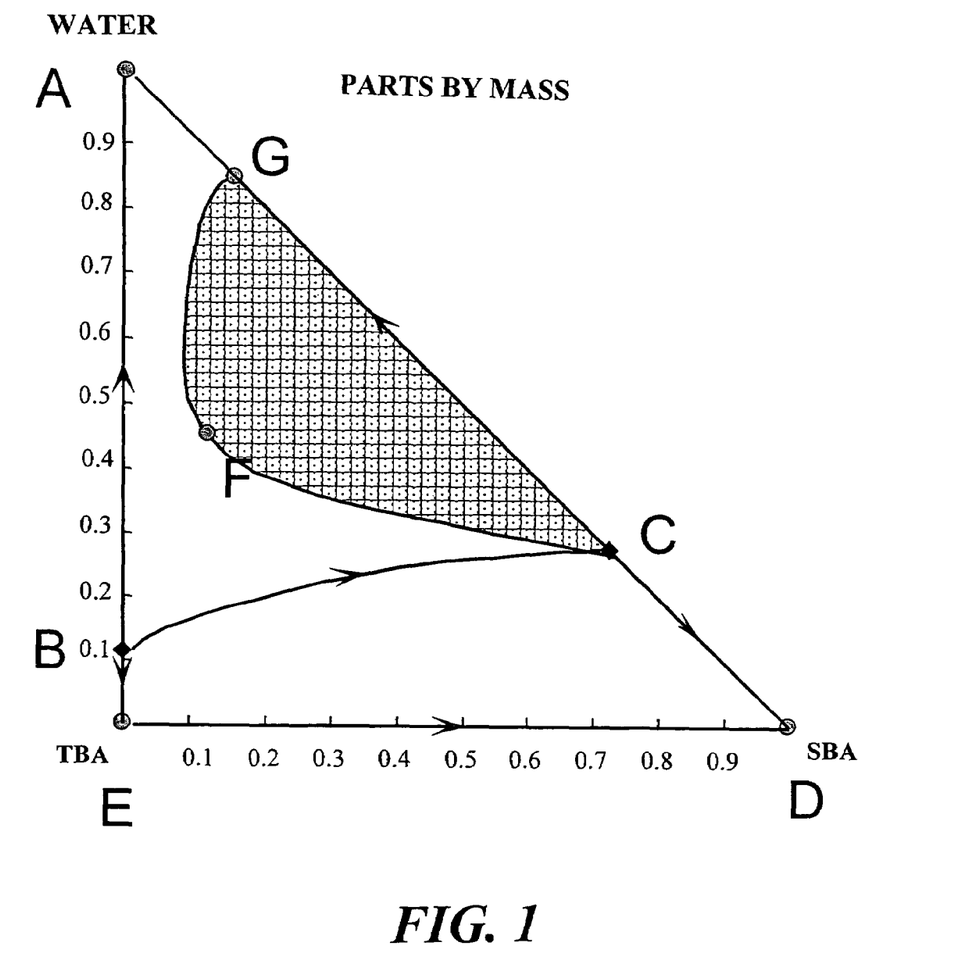
FIG. 1 depicts relative SBA, TBA, and water, in parts by mass, and the azeotropes water/T and water/SBA in a distillation of a mixture containing SBA, TBA, and water. Distillation boundary lines which defined distillation fields 1 and 2 are indicated.

In a process for separating SBA from mixtures of SBA, TBA, and water without losses of TBA, however, it is difficult to separate by distillation since this three-component system displays a distillation boundary line which connects the binary water/TBA azeotrope at about 11% by mass of water (the literature reports values at atmospheric pressure of from 10 to 12.5% by mass) (point B in FIG. 1) and the binary water/SBA azeotrope at about 28% by mass of water (the literature reports values at atmospheric pressure of from 26.7 to 32% by mass) (point C in FIG. 1). This distillation boundary line separates two distillation fields. The above three-component system, shown in FIG. 1, thus displays two distillation fields: distillation field 1 in the region A-B-C-A and distillation field 2 in the region B-E-D-C-B. In the distillation field 1, the high boiler is water, the low boiler in this region is the TBA/water azeotrope and the intermediate boiler is the SBA/water azeotrope which cannot be separated off in pure form.

To discharge SBA from an integrated TBA-isobutene plant, it is most economical to use the stream which is richest in SBA for this purpose. However, the streams obtained in the dissociation of TBA have a relatively low SBA content. They usually have competitions lying in the distillation field 1. These streams usually further comprise small amounts of additional substances whose presence need not, however, be considered in this context. If an attempt is made to work up such a mixture having a composition in the region of distillation field 1 by distillation, it is possible either to isolate pure water as high boiler and a mixture of SBA/TBA/water as top fraction or else obtain the TBA/water azeotrope as lowest-boiling mixture in the distillate from a column and obtain a higher-boiling mixture comprising SBA/TBA/water with a high water content at the bottom. Thus, for mass balance regions and owing to the unfavorable position of the distillation lines, the SBA content cannot be increased sufficiently for discharge of this stream to be economically viable. The miscibility gap in the system (cf. FIG. 1: C-F-G-C) can also not be used economically for separation of the components or increasing their concentration.

SUMMARY OF THE INVENTION

It has surprisingly been found that SBA can be separated off from a production stream which comprises water, SBA and TBA and whose composition lies in the region of distillation field 1, in particular a production stream which is enriched in SBA, virtually without losses of TBA when water is separated off from the production stream used as feed mixture by means of a membrane in such an amount that the retentate has a composition lying in the region of the distillation field 2 and the retentate can thus be separated into SBA and a TBA/water mixture by distillation.

The invention accordingly provides a process for separating SBA from an industrial mixture which comprises SBA, TBA and water and in which the proportion by mass of water is greater than the limit concentrations of the distillation boundary line connecting the two azeotropes TBA/water and SBA/water, i.e. the SBA/TBA/water composition of the mixture lies in the region of the distillation field 1, wherein water is separated off from the mixture by means of a membrane in such an amount that the retentate has, in terms of its SBA/TBA/water composition, a proportion by mass of water which is less than the limit concentration of the distillation boundary line connecting the two azeotropes TBA/water and SBA/water, i.e. in terms of its SBA/TBA/water composition lies in the region of distillation field 2, and the retentate is separated by distillation into a stream comprising SBA and a stream comprising predominantly TBA and water.

Thus, the SBA is separated off in the process of the invention by means of a combination of water removal using a membrane and distillation of the retentate which has been depleted in water.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

The process of the invention makes it possible to separate SBA from mixtures which comprise SBA, TBA and water and in which the proportion by mass of water is greater than the limit concentrations of the distillation boundary line connecting the two azeotropes TBA/water and SBA/water, so that they cannot be separated purely by distillation. The use of the membrane process enables the use of entrainers or other extraneous substances to be dispensed with, so that a costly removal of these auxiliaries can be avoided and there is no risk of contamination of the products by these auxiliaries during the work-up.

In the process of the invention for separating SBA from an industrial mixture which comprises SBA, TBA and water and in which the proportion by mass of water is greater than the limit concentrations of the distillation boundary line connecting the two azeotropes TBA/water and SBA/water, i.e. the SBA/TBA/water composition of the mixture lies in the region of the distillation field 1, water is separated off from the mixture by means of a membrane in such an amount that the retentate has, in terms of its SBA/TBA/water composition, a proportion by mass of water which is less than the limit concentration of the distillation boundary line connecting the two azeotropes TBA/water and SBA/water, i.e. in terms of its SBA/TBA/water composition lies in the region of distillation field 2, and the retentate is separated by distillation into a stream comprising SBA and a stream comprising TBA and water.

As used herein, "distillation boundary line connecting an azeotrope of tert-butanol and water and an azeotrope of 2-butanol and water" means the line which connects the binary water/TBA azeotrope at about 11% by mass of water (the literature reports values at atmospheric pressure of from 10 to 12.5% by mass) (point B in FIG. 1) and the binary water/SBA azeotrope at about 28% by mass of water (the literature reports values at atmospheric pressure of from 26.7 to 32% by mass) (point C in FIG. 1). This distillation boundary line separates two distillation fields. The above three-component system, shown in FIG. 1, thus displays two distillation fields: distillation field 1 in the region A-B-C-A and distillation field 2 in the region B-E-D-C-B. In the distillation field 1, the high boiler is water, the low boiler in this region is the TBA/water azeotrope and the intermediate boiler is the SBA/water azeotrope which cannot be separated off in pure form.

The separation of the water from the SBA-containing feed mixture by means of a membrane can be carried out by reverse osmosis (retentate and permeate are liquid), by pervaporation (liquid retentate, gaseous permeate) or by vapor permeation (retentate and permeate are gaseous). It can also be separated off by simultaneous pervaporation and vapor permeation. The removal of the water by means of a membrane according to the invention is preferably carried out by pervaporation (liquid retentate, gaseous permeate).

The removal of water by reverse osmosis, pervaporation or vapor permeation can be carried out using commercial hydrophilic membranes. These membranes can be polymer membranes or inorganic membranes.

In the process of the invention, it is possible to use, for example, polymer membranes from Sulzer Chemtech, CM-Celfa, GKSS or Sophisticated Systems (polyimide membrane). Types which can be used are, for example, Pervap 2200, Pervap 2201, Pervap 2202 or Pervap 2510 from Sulzer or 2S-DP-H018 from Sophisticated Systems. Examples of inorganic membranes which can be used are: SMS (Sulzer Chemtech); Silica (Pervatech); NaA (Mitsui or Smart Chemical). It is also possible to use combinations of an inorganic membrane or inorganic support material and a polymer membrane or applied polymer separation layer. Inorganic membranes can offer advantages since they are often stable at relatively high temperatures and can more readily be operated using superheated steam. Their stability to organic components can in some cases likewise be higher. On the other hand, polymer membranes offer the advantage that they do not have any catalytic properties, e.g. for polymerization reactions, as can be the case for inorganic membranes.

The removal of water according to the invention using inorganic membranes is preferably carried out at a temperature of from 20 to 200° C. and when using polymer membranes is preferably carried out at a temperature of from 20 to 150° C. The removal of water is particularly preferably carried out at a temperature of from 60 to 140° C. regardless of the type of membrane.

The process of the invention is preferably carried out at a pressure of the mixture fed to the membrane unit (liquid, gaseous or as a mixed phase) of from 0.5 to 30 bar, preferably from 0.8 to 20 bar. The pressure on the permeate side of the membrane is preferably from 0.001 to 1 bar.

In the case of polymer membranes, the differential pressure is preferably from 0.01 to 20 bar and in the case of inorganic membranes it is preferably from 0.01 to 30 bar. The differential pressures are particularly preferably in the range from 1 to 5 bar. The mass flow (kg of permeate per square meter of membrane surface per hour) is preferably from 0.1 to 10 kg/(m2h), particularly preferably from 1 to 8 kg/(m2h). The water separated off as permeate preferably has a content of organic constituents of less than 10% by mass, preferably less than 5% by mass and very particularly preferably from 3 to 0.05% by mass, in particular of TBA.

Smaller values down to 0.001% by mass can also be achieved, but this is usually not necessary and not economically viable.

TBA and SBA can be separated off together from the aqueous permeate to leave pure or virtually pure water. This separation can, for example, be carried out purely by distillation, since the mixture has a composition in the region of distillation field 1 and pure or virtually pure water can be obtained as high boiler and a mixture of SBA/TBA/water can be obtained as top fraction in a distillation. The mixture obtained as top fraction can be recirculated either in its entirety or in part after discharge of a substream to the membrane module for water to be separated off again.

If appropriate, all of some of the permeate can be used directly, for example as process water in a plant for synthesizing TBA.

In terms of its water content, the retentate lies in the distillation field 2, i.e. has a proportion by mass of water which is less than the water content of a mixture having a composition corresponding to the distillation boundary line B-C connecting the azeotropes SBA/water and TBA/water. The water content based on the three-component system SBA/TBA/water at SBA contents of from 0.0001 to 6% by mass is preferably less than 11% by mass, preferably less than 10% by mass and particularly preferably less than 9.5% by mass. At SBA contents of from 6.01 to 15% by mass, the water content based on the three-component system SBA/TBA/water is preferably less than 15% by mass, more preferably less than 14% by mass and particularly preferably less than 13% by mass. In addition, the retentate can further comprise up to 5% by mass, preferably up to 3% by mass, very particularly preferably from 2.5 to 0.01% by mass, of additional substances, for example C8-olefins or C8-alcohols.

The fractional distillation of streams obtained in the process of the invention, in particular the retentate, can be carried out in one or more columns provided with internals which may be trays, rotating internals, random packing and/or ordered packing. The separation by distillation is preferably carried out in a single column.

In the case of column trays, the following types can be used:
trays having holes or slits in the plate;
trays having necks or chimneys which are covered by bills, caps or hoods;
trays having holes covered by movable valves in the plate;
trays having a special construction.

In columns having rotating internals, the runback is either sprayed by means of rotating funnels or is spread as a film over a heated tube wall by means of a rotor.

Disordered beds of various packing elements can be used in the columns employed in the process of the invention. They can be made of virtually any materials, e.g. steel, stainless steel, copper, carbon, stoneware, porcelain, glass, plastics, etc., and have various shapes, e.g. spheres, rings having smooth or profiled surfaces, rings having internal webs or holes in the wall, wire mesh rings, saddles and spirals.

Packing having a regular geometry can comprise, for example, sheets or woven meshes of metal or plastic. Examples of such packing are Sulzer Gewebepackungen BX, Sulzer Lamellenpackungen Mellapak made of sheet metal, high-performance packing such as MellapakPlus, structured packing from Sulzer (Optiflow), Montz (BSH) and Kühni (Rombopak).

The column used for separation of the retentate obtained from the membrane module preferably has from 5 to 70 theoretical plates, preferably from 10 to 60 theoretical plates. The inflow plate depends on the composition of the retentate. It has been found to be advantageous for the retentate to be fed onto the 2nd to 55th, counted from the top, theoretical plate, in particular onto the 3rd to 35th theoretical plate.

The operating pressure of the column for fractionation of the retentate is preferably from 0.1 to 15 barabs. (bara), particularly preferably from 0.8 to 10 bara.

Distillation of the retentate gives a bottom product comprising 2-butanol and possibly high boilers. The TBA content of this stream is preferably less than 1% by mass, more preferably less than 0.5% by mass. A mixture of TBA, water and any low boilers is taken off at the top. The 2-butanol content of the top product is preferably less than 4% by mass, in particular less than 3% by mass. 2-Butanol which is free or virtually free of high boilers can be obtained by taking off the 2-butanol from the vapor phase of the vaporizer or in gaseous or liquid form as side stream in the stripping section of the column.

The TBA fractions separated from the mixture by means of the process of the invention can be employed for known purposes. For example, they can serve as starting material for the preparation of isobutene. Any low boilers present therein can be separated off by distillation.

The 2-butanol which has been separated off can be utilized for customary industrial applications. Thus, for example, it can be used as precursor for methyl ethyl ketone, as solvent for surface coatings and resins, as a constituent of brake fluids and as a constituent of cleaners. Furthermore, it is employed in the production of fragrances, dyes and wetting agents.

The process of the invention enables 2-butanol to be separated off from any ternary mixtures of TBA, SBA and water lying in the distillation field 1 without losses of TBA. This succeeds even when the mixtures further comprise up to 5% by mass of high boilers (e.g. C8- or C12-hydrocarbons formed by oligomerization of isobutene, C8-alcohols) and/or low boilers (e.g. isobutene or other C4-hydrocarbons). Thus, 2-butanol, in particular 2-butanol having a tert-butanol content of less than 1% by mass, preferably less than 0.5% by mass, can be prepared by means of the process of the invention.

In particular, TBA streams enriched in 2-butanol from plants in which isobutene is prepared from TBA by elimination of water are used in the process of the invention. These streams usually further comprise C4-hydrocarbons and downstream products of C4-olefins as additional components.

Figure 2:
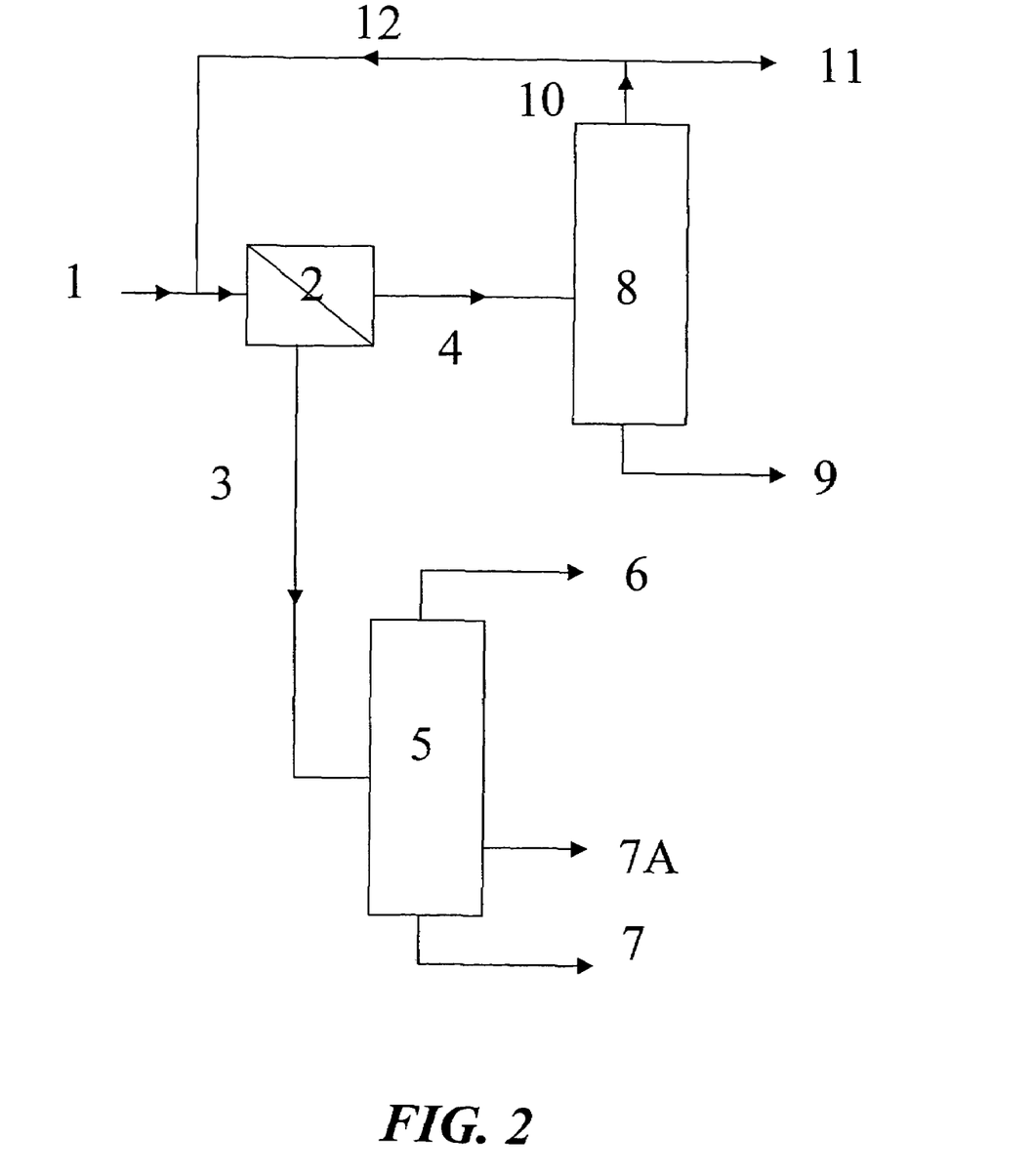
FIG. 2 depicts a block diagram of one embodiment of a plant in which a specific embodiment of the process of the invention can be carried out.

A block diagram of a plant in which the process of the invention can be carried out is shown in FIG. 2. The feed mixture (1) together with an optional part (12) of the distillate (10) from column (8) is fed into the membrane unit (2). The retentate (3) which has been depleted in water is separated in the column (5) into a top product (6) comprising TBA, water, small amounts of SBA and possibly low boilers and a bottom product (7) comprising the 2-butanol to be separated off. To obtain 2-butanol having a low content of high boilers, this product can be taken off from the vapor phase of the vaporizer or in gaseous or liquid form as a side stream (7A) from the stripping section of the column (5). In the column (8), the aqueous permeate (4) is separated into a water stream (9) and a top product (10) comprising TBA, SBA, water and any low boilers. This top product can be recirculated to the membrane unit (2) in its entirety or in part after separating off a substream (11). As an alternative, the permeate stream (4) can be directly used further as process water in a TBA synthesis plant. In this case, the column (8) is not necessary and is omitted.

In another embodiment of the process of the invention, water is removed from the industrial mixture by distillation before it is fed to the membrane unit. Distillation of the industrial mixture separates it into a water-rich bottom product and a top product having a water content which is greater than the limit concentration of the distillation boundary line connecting the two azeotropes TBA/water and SBA/water, i.e. in terms of its SBA/TBA/water composition lies in the region of the distillation field 1, but is below the original water content. The industrial mixture which has been pretreated in this way is then depleted further in water in a membrane unit and is appropriately worked up.

Figure 3:
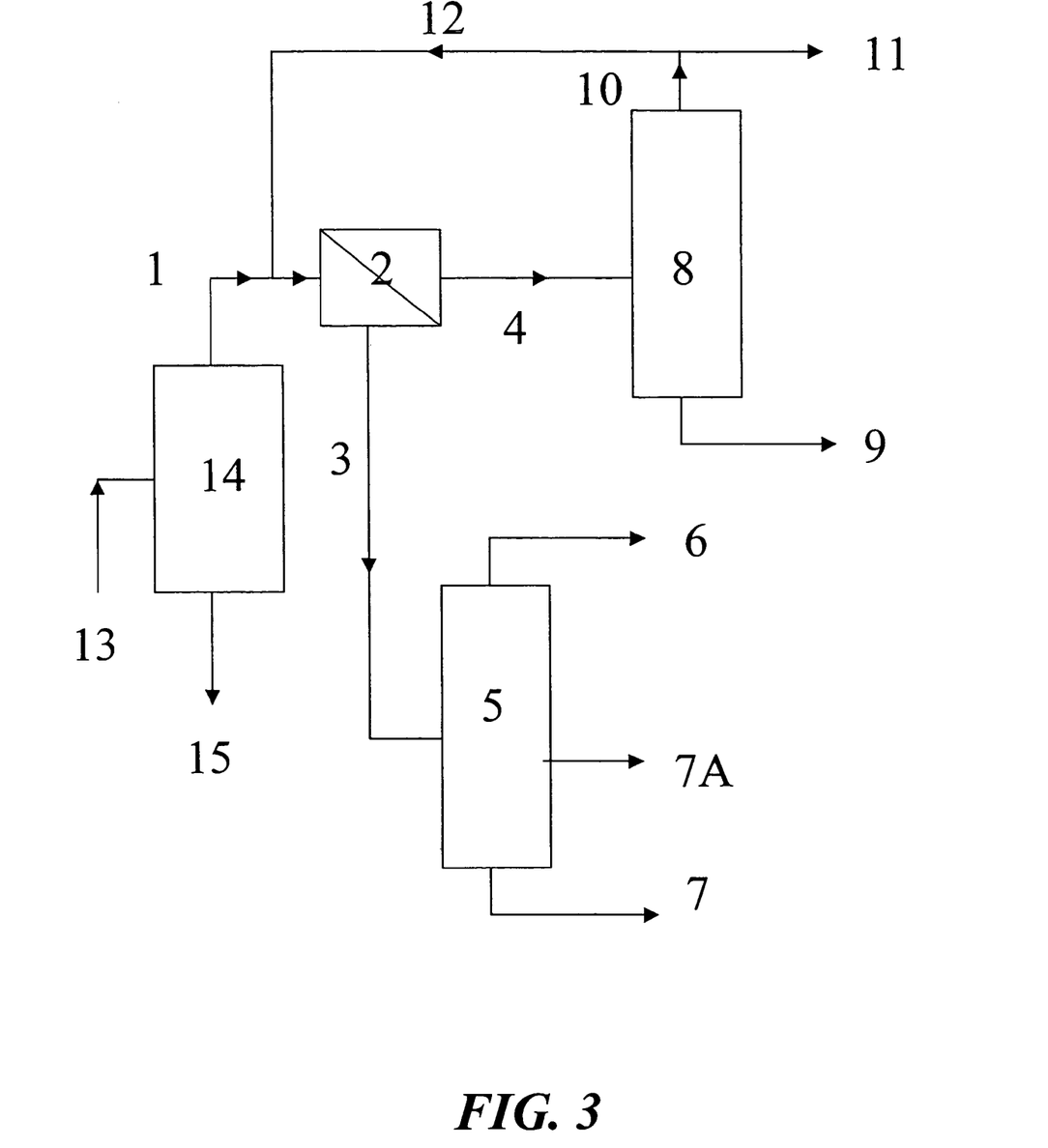
FIG. 3 depicts a block diagram of one embodiment of a plant in which a specific embodiment of the process of the invention can be carried out.

A block diagram of a variant of the plant in which this embodiment of the process of the invention can be carried out is shown in FIG. 3. The feed mixture (13) is firstly worked up in a column (14) to discharge a water-rich stream (15) at the bottom of the column. The distillate stream (1) which has been partly dewatered in this way is then introduced together with an optional part (12) of the distillate (10) from the column (8) into the membrane unit (2). The water-depleted retentate (3) is separated in the column (5) into a top product (6) comprising TBA, water and any low boilers and a bottom product (7) comprising the 2-butanol to be separated off. In this case too, the product can be taken off from the vapor phase of the vaporizer or in gaseous or liquid form as side stream (7A) from the stripping section of the column (5) in order to be able to obtain 2-butanol having a low content of high boilers. The aqueous permeate (4) is separated in the column (8) into a water stream (9) and a top product (10) comprising TBA, SBA, water and any low boilers. This top product can be recirculated to the membrane unit (2) in its entirety or in part after separating off a substream (11). As an alternative, the permeate stream (4) can be directly used further as process water in a TBA synthesis plant. In this case, the column (8) is not necessary and is omitted.

The advantage of this variant is that the concentration of water in the feed (1) to the membrane unit is reduced in the preliminary dewatering column (14) so that the composition of this feed in the distillation field 1 moves closer to the distillation boundary line BC. This means that less water has to be separated off from the feed stream (1) in the membrane unit in order to bring the concentration into the distillation field 2, so that the membrane module can be made smaller and is cheaper to construct.

As preliminary dewatering column, it is possible to use a column customarily used for distillation. This column preferably has from 5 to 70 theoretical plates, preferably from 10 to 60 theoretical plates. The inflow plate depends on the composition of the feed. It has been found to be advantageous for the feed to be fed in onto the 2nd to 55th theoretical plate, counted from the top, in particular onto the 3rd to 35th theoretical plate. The operating pressure of the preliminary dewatering column is preferably from 0.1 to 15 barabs. (bara), particularly preferably from 0.8 to 10 bara.

In a further embodiment of the process of the invention, the mixture to be separated is introduced as feed into a column in which water is discharged as side stream by means of a membrane module and the retained mixture which has been depleted in water is returned to the column. Distillation of this mixture separates it into a TBA-enriched top product and a water-enriched product having a water content which is greater than the limit concentration of the distillation boundary line connecting the two azeotropes TBA/water and SBA/water, i.e. in terms of its SBA/TBA/water composition lies in the region of the distillation field 1, in the middle of the column. This water-rich mixture is taken off from the distillation column in gaseous or liquid form as a side stream from below the feed point and is transferred to a membrane module. In this, the water-rich product is concentrated according to the invention by discharge of water as permeate to bring it to a water content which is less than the limit concentration of the distillation boundary line connecting the two azeotropes TBA/water and SBA/water. This retentate which has been depleted in water is returned to the lower part of the column by feeding it in at the same point or a lower point (relative to the position of the point at which the side stream is taken off), as a result of which the mixture in the lower part of the column has an SBA/TBA/water composition in which the proportion by mass of water is less than the limit concentration of the distillation bounary line connecting the two azeotropes TBA/water and SBA/water and enriched SBA can be separated off at the bottom of the column.

Figure 4:
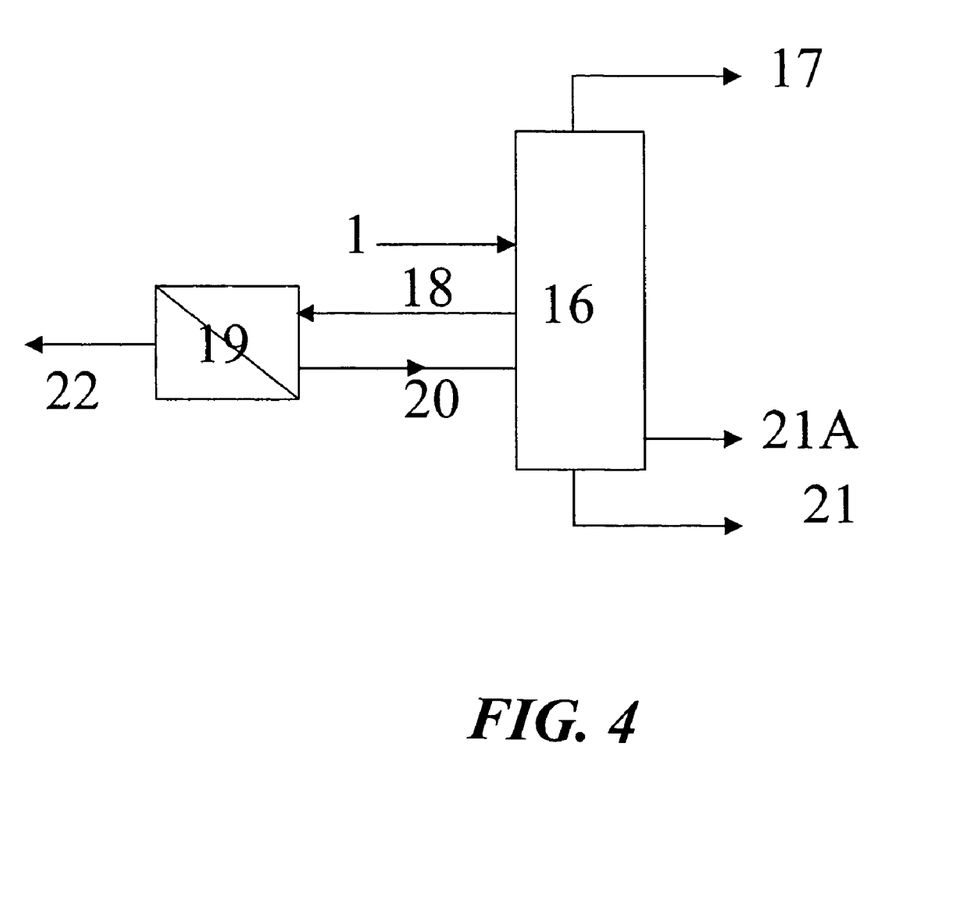
FIG. 4 depicts a block diagram of one embodiment of a plant in which a specific embodiment of the process of the invention can be carried out.

A block diagram of a variant of the plant in which this embodiment of the process of the invention can be carried out is shown in FIG. 4. The feed mixture (1) is introduced into the upper part of a column (16) and worked up there so as to give a TBA-rich stream (17) at the top of the column. Below the feed point, a gaseous or liquid side stream (18) is taken off and is fed into the membrane unit (19). The retentate (20) which has been depleted in water is fed back into the column (16) at the same point or a lower point (number of theoretical plates from the top downward). In the part below this recirculation point, the composition is in the distillation field 2 and a bottom product (21) comprising the 2-butanol to be separated off can be obtained. In this case too, the product can be taken off from the vapor phase of the vaporizer or in gaseous or liquid form as side stream (21A) from the stripping section of the column (16) in order to be able to obtain 2-butanol having a low content of high boilers. The aqueous permeate (22) is continuously discharged from the membrane module, with the amount of water discharged being such that the composition of the retentate obtained is in the distillation field 2. The water can be reused as process water in a TBA synthesis plant. As an alternative, the permeate (22) can be worked up in a subsequent distillation so as to give pure water as bottom product and a top stream comprising predominantly TBA, other organic components and small amounts of water.

Advantages of this variant are that only one column is needed and it is not necessary for the stream (18) to be dewatered completely in the membrane module, but instead it is only necessary to remove such an amount of water that the composition moves from the distillation field 1 to the distillation field 2. As a result, the membrane area required is smaller and the membrane module can be constructed more cheaply.

For the fractional distillation, it is possible to use industrial columns whose possible construction types have already been described on preceding pages, in particular in the description of the fractional distillation of the streams obtained in the process of the invention. The column preferably has from 5 to 120 theoretical plates, preferably from 10 to 90 theoretical plates. The feed plate depends on the composition of the feed. It has been found to be advantageous for the feed to be introduced onto the 2nd to 85th theoretical plate, counted from the top, in particular onto the 3rd to 75th theoretical plate. The gaseous or liquid side stream is taken off below the feed point at the 3rd to 110th theoretical plate, counted from the top, preferably at the 4th to 95th theoretical plate, and the stream (20) which has been depleted in water is returned to the column (16) at the 3rd to 111th theoretical plate, preferably the 5th to 96th theoretical plate. The operating pressure of the column in this embodiment of the process of the invention is preferably from 0.1 to 15 barabs. (bara), particularly preferably from 0.8 to 10 bara.

Customary components such as pumps, compressors, valves, heat exchangers and vaporizers are not shown in the block diagrams, but are of course components of a plant.

The following examples illustrate the invention without restricting its scope which is defined by the description and the claims.

EXAMPLE 1

SBA was separated off in a plant of the type shown in FIG. 2 with the column (8) and thus the streams 9, 10, 11 and 12 being omitted. The diameter of the column (5) was 50 mm. Metal distillation packing having 20 theoretical plates was installed, and the feed was introduced onto the 5th theoretical plate counted from the top. The feed (1) used for the experiments was taken from an industrial plant for the preparation of isobutene and had the composition indicated in table 1. It was fed in gaseous form into the membrane module with the aid of a prevaporizer. The membrane treatment was carried out as a vapor permeation in an experimental laboratory plant using a Sulzer 2201 membrane from Sulzer. The stream numbers in the following table correspond to those in FIG. 2. Components having a concentration below 0.1 parts by mass in the mixture are generally not shown in the table.

TABLE 1

| Stream number | Stream name | Mass flow [kg/h] | Concentration of the components to be separated off, in parts by mass | |
|---|---|---|---|---|
| 1 | Fresh feed | 3.66 | Water | 62.0 |
| | | | TBA | 33.7 |
| | | | 2-Butanol | 3.4 |
| | | | C8-Alcohol | 0.7 |
| | | | Other components | 0.2 |
| 3 | Retentate | 1.50 | Water | 9.1 |
| | | | TBA | 80.7 |
| | | | 2-Butanol | 8.0 |
| | | | C8-Alcohol | 1.8 |
| | | | Other components | 0.4 |

TABLE 1-continued

| Stream number | Stream name | Mass flow [kg/h] | Concentration of the components to be separated off, in parts by mass | |
|---|---|---|---|---|
| 4 | Permeate | 2.16 | Water | 98.7 |
| | | | TBA | 1.1 |
| | | | 2-Butanol | 0.1 |
| | | | Other components | 0.1 |
| 6 | Distillate from column (5) | 1.38 | Water | 9.9 |
| | | | TBA | 88.0 |
| | | | 2-Butanol | 2.0 |
| | | | Other components | 0.1 |
| 7 | Bottoms from column (5) | 0.12 | TBA | 0.1 |
| | | | 2-Butanol | 75.5 |
| | | | C8-Alcohol | 21.7 |
| | | | Other components | 2.7 |

The pressure of the distillate stream (1) on the feed side of the membrane was 1 bar and the pressure on the permeate side (4) of the membrane was 0.055 bar. The column (5) was operated at 1 barabs. and a reflux ratio of 10.

EXAMPLE 2

SBA was separated off in a plant of the type shown in FIG. 3 with the column (14) being operated separated from the remainder of the plant. The diameter of the column (14) was 50 mm. Metal distillation packing having 10 theoretical plates was installed, and the feed was introduced onto the 5th theoretical plate counted from the top. The feed (13) used for the experiments was taken from an industrial plant for the preparation of isobutene and had the composition indicated in table 2. The resulting distillate which had been depleted in water was collected and the concentration of water was subsequently reduced further in the vapor permeation. The vapor permeation was carried out in an experimental laboratory plant using a Sulzer 2201 membrane from Sulzer. The column (5) corresponded to the construction in example 1, but the SBA was taken off as a side stream (7A) from the packing above the vaporizer with the aid of a liquid collector. The region between the vaporizer and the liquid offtake was provided with distillation packing corresponding to about 1 theoretical plate. Column (8) was omitted, so that the streams 9, 10, 11 and 12 were also absent. The stream numbers in table 2 below refer to the numbering of the steams in FIG. 3. Components having a concentration below 0.1 parts by mass in the mixture are generally not shown in table 2.

TABLE 2

| Stream number | Stream name | Mass flow [kg/h] | Concentration of the components to be separated off (parts by mass) | |
|---|---|---|---|---|
| 13 | Fresh feed | 25 | Water | 96.6 |
| | | | TBA | 3.0 |
| | | | 2-Butanol | 0.3 |
| | | | C8-Alcohol | 0.1 |
| 15 | Wastewater | 23.72 | Water | 99.9 |
| | | | TBA | 0.1 |

TABLE 2-continued

| Stream number | Stream name | Mass flow [kg/h] | Concentration of the components to be separated off (parts by mass) | |
|---|---|---|---|---|
| 1 (as distillate) | Distillate | 1.28 (was collected for membrane experiments) | Water<br>TBA<br>2-Butanol<br>C8-Alcohol<br>Other components | 34.6<br>58.3<br>5.8<br>1.0<br>0.3 |
| 1 (as starting material) | Feed to membrane | Collected product: 3.93 | Water<br>TBA<br>2-Butanol<br>C8-Alcohol<br>Other components | 34.6<br>58.3<br>5.8<br>1.0<br>0.3 |
| 3 | Retentate | 2.60 | Water<br>TBA<br>2-Butanol<br>C8-Alcohol<br>Other components | 3.1<br>86.3<br>8.6<br>1.5<br>0.5 |
| 4 | Permeate | 1.33 | Water<br>TBA<br>2-Butanol<br>C8-Alcohol | 96.1<br>3.4<br>0.3<br>0.1 |
| 6 | Distillate from column (5) | 2.34 | Water<br>TBA<br>2-Butanol<br>Other components | 3.5<br>95.7<br>0.6<br>0.2 |
| 7A | Side stream from column (5) | 0.19 | TBA<br>2-Butanol<br>C8-Alcohol<br>Other components | 0.6<br>98.8<br>0.4<br>0.2 |
| 7 | Bottoms from column (5) | 0.06 | TBA<br>2-Butanol<br>C8-Alcohol<br>Other components | 0.1<br>31.6<br>58.8<br>9.5 |

The pressure of the distillate stream (1) on the feed side of the membrane was 1 bar and the pressure on the permeate side (4) of the membrane was 0.055 bar. The column (5) was operated at 1 barabs. and a reflux ratio of 5. The column (14) was operated at a pressure of 1 barabs. and a reflux ratio of 2.8.

Obviously, numerous modifications and variations of the present invention are possible in light of the above teachings. It is therefore to be understood that within the scope of the appended claims, the invention may be practiced otherwise than as specifically described herein.

This application claims priority to DE 10312916.2, which was filed Mar. 22, 2003, the entire contents of which are incorporated herein by reference.

The invention claimed is:

1. A process for separating 2-butanol from an industrial mixture which comprises 2-butanol, tert-butanol, and water wherein the proportion by mass of water is greater than the limit concentration of the distillation boundary line connecting an azeotrope of tert-butanol and water; and an azeotrope of 2-butanol and water, comprising separating water from the industrial mixture with a membrane to obtain a retentate which comprises a proportion by mass of water, in terms of the 2-butanol, tert-butanol and water in the retentate, is less than the limit concentration of the distillation boundary line connecting connecting an azeotrope of tert-butanol and water; and an azeotrope of 2-butanol and water; and the separating the retentate by distillation into a stream comprising 2-butanol and a stream comprising tert-butanol and water.

2. The process as claimed in claim 1, wherein the separating the water comprises pervaporation.

3. The process as claimed in claim 1, wherein the separating the water comprises vapor permeation.

4. The process as claimed in claim 1, wherein the separating the water comprises pervaporation and vapor permeation.

5. The process as claimed in claim 1, which further comprises removing water from the industrial mixture by distillation before separating water with the membrane.

6. The process as claimed in claim 1, wherein the separating water from the industrial mixture with the membrane is conducted at a temperature from 60 to 140° C.

7. The process as claimed in claim 1, wherein the membrane is an inorganic membrane.

8. The process as claimed in claim 7, wherein the separating water from the industrial mixture with the inorganic membrane is conducted at a temperature from 20 to 200° C.

9. The process as claimed in claim 1, wherein the membrane is a polymer membrane.

10. The process as claimed in claim 9, wherein the separating water from the industrial mixture with the polymer membrane is conducted at a temperature from 20 to 150° C.

11. The process as claimed in claim 1, wherein the membrane comprises a combination of one of an inorganic membrane or and inorganic support material; and one of a polymer membrane or applied polymer separation layer.

12. The process as claimed in claim 1, wherein the retentate has a water content of less than 10% by mass, based on the 2-butanol, tert-butanol and water in the retentate.

13. The process as claimed in claim 1, wherein the stream comprising 2 contains less than 1% by mass of tert-butanol.

14. The process as claimed in claim 1, wherein the proportion of water in the retentate is less than 11% by mass when the concentration of 2-butanol is from 0.0001 to 6% by mass.

15. The process as claimed in claim 14, wherein the proportion of water in the retentate is less than 10% by mass.

16. The process as claimed in claim 14, wherein the proportion of water in the industrial mixture is less than 9.5% by mass.

17. The process as claimed in claim 1, wherein the proportion of water in the industrial mixture is less than 15% by mass when the concentration of 2-butanol is from 6.01 to 15% by mass.

18. The process as claimed in claim 17, wherein the proportion of water in the industrial mixture is less than 14% by mass.

19. The process as claimed in claim 17, wherein the proportion of water in the industrial mixture is less than 13% by mass.

20. The process as claimed in claim 1, wherein the industrial mixture is a side stream discharged from a distillation column in gaseous or liquid form, wherein the side stream is fed to the membrane whereby water is discharged through the membrane as permeate and the retentate is fed back into the column at the point where at the same or different points in the distillation column where the industrial mixture side stream is discharged, and the stream comprising 2-butanol is separated off at a bottom portion of the column.

* * * * *